US00RE38131E

(19) United States
(12) Reissued Patent
Uchihashi et al.

(10) Patent Number: US RE38,131 E
(45) Date of Reissued Patent: Jun. 3, 2003

(54) REAGENT FOR MEASUREMENT OF LEUKOCYTES AND HEMOGLOBIN CONCENTRATION IN BLOOD

(75) Inventors: Kinya Uchihashi, Kakogawa (JP); Yoshiro Ikeuchi, Kobe (JP); Atsushi Shirakami, Miki (JP); Yukio Hamaguchi, Akashi (JP)

(73) Assignee: Sysmex Corporation, Kobe (JP)

(21) Appl. No.: 09/977,768

(22) Filed: Oct. 15, 2001

Related U.S. Patent Documents

Reissue of:
(64) Patent No.: 5,968,832
Issued: Oct. 19, 1999
Appl. No.: 09/057,250
Filed: Apr. 8, 1998

(30) Foreign Application Priority Data

Apr. 18, 1997 (JP) ..... 9-101808

(51) Int. Cl.[7] ..... G01N 31/00; G01N 33/72
(52) U.S. Cl. ..... 436/10; 436/8; 436/17; 436/18; 436/63; 436/66; 436/174; 436/175; 436/176; 252/408.1
(58) Field of Search ..... 436/8, 10, 17, 436/15, 18, 63, 66, 174, 175, 176; 252/408.1; 435/2

(56) References Cited

U.S. PATENT DOCUMENTS

| | | | | |
|---|---|---|---|---|
| 4,185,964 | A | 1/1980 | Lancaster | 436/17 |
| 5,242,832 | A | 9/1993 | Sakata | 436/17 |
| 5,250,437 | A | 10/1993 | Toda et al. | 436/10 |
| 5,389,549 | A | 2/1995 | Hamaguchi et al. | 436/10 |
| 5,618,733 | A | 4/1997 | Sakata et al. | 436/17 |
| 5,639,630 | A | 6/1997 | Malin et al. | 435/28 |
| 5,686,308 | A | 11/1997 | Li et al. | 436/63 |
| 5,786,224 | A | 7/1998 | Li et al. | 436/63 |
| 5,834,315 | A | 11/1998 | Riesgo et al. | 436/66 |
| 5,843,608 | A | 12/1998 | Li et al. | 436/63 |

FOREIGN PATENT DOCUMENTS

| | | |
|---|---|---|
| EP | 0 444 241 | 9/1991 |
| EP | 0 794 435 | 9/1997 |
| WO | WO 84/04969 | 12/1984 |

*Primary Examiner*—Maureen M. Wallenhorst
(74) *Attorney, Agent, or Firm*—Pearne & Gordon LLP

(57) ABSTRACT

A reagent for measurement of leukocytes and hemoglobin concentration in the blood includes a cationic surfactant in an amount sufficient to lyse erythrocytes and denature hemoglobin, at least one of the following hemoglobin stabilizers:

(a) sulfosalicylic acid, or its salt, in an amount effective for promoting the conversion of hemoglobin into methemoglobin, (b) 0.2 to 10.0 g/L of a water-soluble chelating agent having a nitrogen atom and a carboxyl group, and (c) piperazine, or its salt, in an amount effective for promoting the conversion of hemoglobin into methemoglobin, and a buffer for maintaining pH at 4 to 6.

6 Claims, 3 Drawing Sheets

REAGENT FOR MEASUREMENT OF LEUKOCYTES AND HEMOGLOBIN CONCENTRATION IN BLOOD

Matter enclosed in heavy brackets [ ] appears in the original patent but forms no part of this reissue specification; matter printed in italics indicates the additions made by reissue.

BACKGROUND OF THE INVENTION

This invention relates to a reagent for measurement of leukocytes and hemoglobin concentration in a blood sample.

Measuring the leukocyte count and hemoglobin concentration in the blood is very important for the clinical diagnosis of leukemia, anemia, etc. or for monitoring the clinical course in patients.

Currently, the leukocyte count and hemoglobin concentration can be measured in a short time by an automatic blood analyzer, and such an analyzer is in widespread use.

Automatic blood analyzers can be roughly classified into an optical detection system for detecting light scattering or fluorescence, and an electric resistance detection system for detecting a change in impedance occurring when particles pass through an aperture. The latter system is superior in terms of ease of use. According to the electric resistance detection system, the measurement of the leukocyte count is performed by adding a hemolytic agent to a blood sample to lyse erythrocytes and prepare a sample for leukocyte measurement with only leukocytes left, and then flowing this sample through a detector to detect a signal issued.

Normally, leukocytes in the peripheral blood include five types of cells, lymphocyte, monocyte, neutrophil, eosinophil and basophil. By formulating the hemolytic agent in a preferred manner, it becomes possible to classify the leukocytes into 2 or 3 populations, or detect only leukocytes of a particular type. Thus, leukocyte classification that has necessarily relied on microscopic observation can be performed automatically in a short time. This has reduced the burden on laboratory technicians, and has obviated the need for special technique for laboratory examination.

To measure hemoglobin concentrations, on the other hand, it has been adopted as the international standard method to convert hemoglobin into cyanmethemoglobin by the use of Van Kampen reagent containing a cyanogen compound, and measuring its absorbance at about 541 nm. For an automatic blood cell analyzer, a method is known which fragments erythrocytes, and denatures hemoglobin, with a quaternary ammonium salt having surface activity, obtains a cyanmethemoglobin-like absorption curve with the use of an alkali cyanide, and determines hemoglobin as well as leukocytes. However, harmful cyanogen compounds are contained in the reagents. These reagents or the samples after measurement need to be subsequently made atoxic before being discarded.

There is a known reagent which permits leukocyte counting without using a cyanogen compound for the determination of the hemoglobin concentration (U.S. Pat. No. 4,185,964). This reagent contains a water-soluble quaternary ammonium salt having surface activity, and a small amount of a polycarboxylic acid having up to about 8 carbon atoms in an amount sufficient to inhibit the lysis of leukocytes. Hemolytic agents which enable leukocytes to be classified into three populations are also known. These hemolytic agents contain quaternary ammonium salts and specific hemoglobin stabilizers (Japanese Unexamined Patent Publication Nos. 3-137566, 3-252557 and 4-13969).

The above hemolytic agents can denature hemoglobin rapidly, but have the drawback that the hemoglobin concentration markedly varies with the liquid temperature of the blood sample. Particularly in U.S. Pat. No. 4,185,964, the variations are great, since no stabilizer is used. In Japanese Unexamined Patent Publication Nos. 3-137566, 3-252557 and 4-13969, specific hemoglobin stabilizers are incorporated, so that the variations are reduced. However, when the liquid temperature fluctuates, the hemoglobin concentration also fluctuates. The stabilizing effect of these stabilizers is insufficient in this case. To obtain stable measurements, therefore, a unit for keeping the liquid temperature constant is required. This is one of the factors leading to an increase in the cost of the apparatus.

SUMMARY OF THE INVENTION

An object of the present invention is to provide a reagent which does not use a cyanogen compound, can measure the leukocyte count, and can also measure the hemoglobin concentration stably even when the liquid temperature of the sample varies.

The reagent for measurement of leukocytes and hemoglobin concentration according to the present invention contains:

(1) a cationic surfactant in an amount sufficient to lyse erythrocytes and denature hemoglobin, (2) at least one hemoglobin stabilizer selected from the group consisting of the following (a), (b) and (c):

(a) sulfosalicylic acid, or its salt, in an amount effective for promoting the conversion of hemoglobin into methemoglobin, (b) 0.2 to 10.0 g/L of a water-soluble chelating agent having a nitrogen atom and a carboxyl group, and (c) piperazine, or its salt, in an amount effective for promoting the conversion of hemoglobin into methemoglobin, and (3) a buffer for maintaining pH at 4 to 6.

The use of the reagent for measurement of leukocytes and hemoglobin concentration according to the present invention enables leukocytes and hemoglobin concentration to be measured simultaneously or separately.

The reagent for measurement of leukocytes and hemoglobin concentration according to the present invention contains a cationic surfactant in an amount sufficient to lyse erythrocytes and denature hemoglobin. The cationic surfactant preferably includes at least one cationic surfactant of the quaternary ammonium salt type or pyridinium salt type having the structure indicated below.

Preferred examples are as follows:

(a) Quaternary ammonium salts

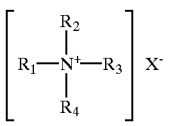

where $R_1$ represents a $C_8$–$C_{20}$ alkyl group, alkenyl group or alkinyl group, $R_2$, $R_3$ and $R_4$ represent, independently of each other, a $C_1$–$C_8$ alkyl group, alkenyl group or alkinyl group, and $X^-$ represents a halogen ion.

(b) Pyridinium salts

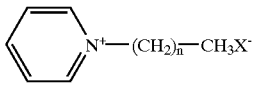

where n denotes an integer of 7 to 19, and $X^-$ represents a halogen ion.

The preferred concentration of the cationic surfactant used in the reagent of the present invention is 0.1 to 15.0 g/L. The preferred cationic surfactant is a quaternary ammonium salt, and the particularly preferable concentration is 0.1 to 4.0 g/L. By suitably combining the surfactants stated above, leukocytes can be classified, for example, into lymphocytes and others, or into lymphocytes, neutrophils and others.

The reagent for measurement of leukocytes and hemoglobin concentration according to the present invention also contains a hemoglobin stabilizer in an amount effective for promoting the conversion of hemoglobin into methemoglobin. The stabilizer is at least one member selected from the group consisting of (a) sulfosalicylic acid or its salt, (b) a water-soluble chelating agent having a nitrogen atom and a carboxyl group, and (c) piperazine or its salt. Examples of the water-soluble chelating agent are ethylenediaminetetraacetic acid or its salts, diaminopropanoltetraacetic acid or its salts, diaminopropanetetraacetic acid or its salts, ethylenediaminediacetic acid or its salts, and ethylenediaminedipropionic acid or its salts. Particularly preferred are ethylenediaminetetraacetates.

The hemoglobin stabilizer is used in an amount effective for promoting the conversion of hemoglobin into methemoglobin. Normally, it is used in a preferred amount in the range of 0.2 to 10.0 g/L. A more preferable concentration differs depending on the substance used. When sulfosalicylic acid or its salt is used, the more preferable concentration is 0.2 to 2.0 g/L. When the water-soluble chelating agent is used, a particularly preferred concentration is 0.5 to 10 g/L for ethylenediaminetetraacetic acid salt, 0.5 to 5 g/L for diaminopropanoltetraacetic acid or its salt, 0.5 to 5 g/L for diaminopropanetetraacetic acid or its salt, 0.5 to 5 g/L for ethylenediaminediacetic acid or its salt, or 0.5 to 5 g/L for ethylenediaminedipropionic acid dihydrochloride. In the case of piperazine or its salt, it is used preferably in a concentration of 0.5 to 5 g/L. When this stabilizer has a buffer action, it may be used as part of the buffer.

These stabilizers are presumed to exhibit their stabilizing effect by binding to the heme of methemoglobin denatured with the aforementioned cationic surfactant or a combination of the cationic surfactants.

The buffer is not restricted as long as it can maintain a pH at 4.0 to 6.0. Too low a pH makes leukocytes fragile, thereby adversely affecting the measurement of the leukocyte count. Too high a pH, on the other hand, results in poor stability of hemoglobin over time. Concretely, known buffers can be used, such as Good buffer, phosphate buffer, succinate buffer, and maleate-TRIS buffer. The concentration of the buffer is 5 to 50 mM, preferably 15 to 30 mM.

The above-mentioned concentrations of the respective components are the concentrations used when the blood is directly diluted with the reagent for measurement of leukocytes and hemoglobin concentration according to the present invention. Alternatively, the reagent may be added after the blood is diluted with a diluent (e.g., physiological saline solution or Cellpack™ (TOA MEDICAL ELECTRONICS CO., LTD.)). In this case, it suffices to adjust the concentrations of the respective components so that after addition of the reagent, these concentrations would fall into the indicated ranges. The above diluent is preferably one with a pH close to neutrality (6 to 8) and an osmotic pressure close to isotonicity (240 to 330 Osm/kg) for maintaining the shape of the blood cells.

The reagent of the present invention has electric conductivity, preferably, of 8 to 20 mS/cm, and more preferably, of 10 to 15 mS/cm. The electric conductivity can be adjusted by suitably adding an electrolyte such as NaCl.

The leukocyte count and the hemoglobin concentration can be measured in the following manner: A blood sample is prepared using the reagent for measurement of leukocytes and hemoglobin concentration according to the present invention. The blood sample is introduced into an automatic blood cell analyzer. In this apparatus, a change in impedance occurring during passage of particles through an aperture is detected to measure the leukocyte count, and the absorbance of the sample is detected to measure the hemoglobin concentration. In this case, the leukocyte count and the hemoglobin concentration can be measured simultaneously or separately.

Formulation examples of the reagent of the present invention are offered below.

FORMULATION EXAMPLE 1

| | |
|---|---|
| Cetyltrimethylammonium chloride | 0.3 to 3.0 g/L |
| EDTA-2K | 0.5 to 5.0 g/L |
| Phosphate buffer | 15 to 30 mM |
| NaCl | Proper amount |
| Purified water | 1 L |

FORMULATION EXAMPLE 2

| | |
|---|---|
| Lauryltrimethylammonium chloride | 0.3 to 10.0 g/L |
| Stearyltrimethylammonium chloride | 0.1 to 1.0 g/L |
| EDTA-2K | 0.5 to 5.0 g/L |
| Good buffer | 15 to 30 mM |
| NaCl | Proper amount |
| Purified water | 1 L |

FORMULATION EXAMPLE 3

| | |
|---|---|
| Lauryltrimethylammonium chloride | 0.3 to 10.0 g/L |
| Lauryldimethylaminoacetate betaine | 0.5 to 5.0 g/L |
| EDTA-2K | 0.5 to 5.0 g/L |
| Succinate buffer | 15 to 30 mM |
| NaCl | Proper amount |
| Purified water | 1 L |

With Formulation Examples 1 to 3, leukocyte and hemoglobin can be measured simultaneously. By adjusting the type and concentration of each surfactant, leukocytes can be classified into two or more populations. The populations of leukocytes refer, for example, to lymphocytes, monocytes, neutrophils, eosinophils and basophils. Formulation Example 1 is a combination of the components designed to classify leukocytes into a single population, while Formulation Examples 2 and 3 are combinations of the components designed to classify leukocytes into two or three populations.

DETAILED DESCRIPTION OF THE PREFERRED EMBODIMENTS

The present invention will now be described by, but not restricted to, the following Examples.

EXAMPLE 1

Stability to Changes in Temperature

The reagent of the present invention and reagents as Controls 1 and 2 to be described below were prepared. Each of the reagents was reacted with a patient's sample at a different temperature, and the hemoglobin concentration was measured.

| Reagent of the Present Invention | |
|---|---|
| Lauryltrimethylammonium chloride | 3.0 g/L |
| Stearyltrimethylammonium chloride | 0.2 g/L |
| EDTA-2K | 1.0 g/L |
| phosphate buffer | 20 mM (pH 5.0) |
| NaCl | Proper amount (the proper amount is such an amount that the electric conductivity is about 13 mS/cm) |
| Purified water | 1 L |
| Control 1 | |
| Lauryltrimethylammonium chloride | 3.0 g/L |
| Stearyltrimethylammonium chloride | 0.2 g/L |
| Phosphate buffer | 20 mM |
| NaCl | Proper amount (the proper amount is such an amount that the electric conductivity is about 13 mS/cm) |
| Purified water | 1 L |
| Control 2 | |
| Lauryltrimethylammonium chloride | 3.0 g/L |
| Stearyltrimethylammonium chloride | 0.2 g/L |
| Imidazole | 1.0 g/L |
| Tris-maleate buffer | (such an amount that the electric conductivity is about 13 mS/cm) |
| Purified water | 1 L |

The blood was diluted 1:500 with each reagent of the above formulation, and reacted for 30 seconds at 10° C. and 35° C. Then, the absorbances were measured with a spectrophotometer, and the change rate of the absorbance at 35° C. to the absorbance at 10° C. was calculated. From this change rate, the amount of changed hemoglobin (converted value) was determined. The results are shown in Table 1.

TABLE 1

| Reagent | Change rate | Amount of changed hemoglobin (converted value) |
|---|---|---|
| Present invention | −3.50% | −0.53 g/dl |
| Control 1 | −15.7% | −2.34 g/dl |
| Control 2 | −6.1% | −0.91 g/dl |

Change rate = Absorbance at 35° C./absorbance at 10° C.

The reagent as Control 1 had the composition of the reagent of the present invention from which the stabilizer was removed. This reagent had a high change rate due to temperature. The reagent of the present invention contained EDTA-2K as the stabilizer, while Control 2 contained imidazole as the stabilizer. Both reagents were lower in change rate than in Control 1 free from the stabilizer.

A stabilizer other than these substances was usable, but the degree of the change rate differed according to the type of the stabilizer used.

EXAMPLE 2

Correlation with a Conventional Method

| Composition of reagent | |
|---|---|
| Lauryltrimethylammonium chloride | 8.7 g/L |
| Stearyltrimethylammonium chloride | 0.8 g/L |
| EDTA-2K | 3.0 g/L |
| Phosphate buffer | 60 mM (pH 5.0) |
| NaCl | Such an amount that the electric conductivity is about 13 mS/cm |
| Purified water | 1 L |

1) Correlation in Hemoglobin Concentration

Figure 1:
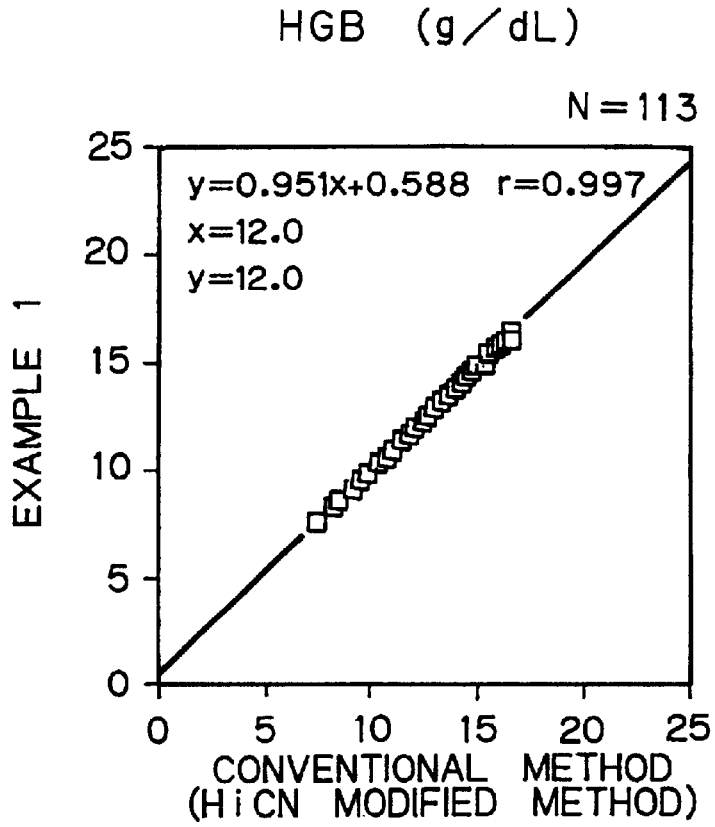
FIG. 1 is a graph showing the correlation between the hemoglobin concentration measured by the use of the reagent of the present invention and the hemoglobin concentration measured by a conventional method.

The hemoglobin concentrations in 113 samples were measured with the use of the above reagent, Cellpack™ (TOA MEDICAL ELECTRONICS CO., LTD.) as a diluent, and K-4500 (TOA MEDICAL ELECTRONICS CO., LTD.). A graph was drawn to show the correlation of the results with the hemoglobin concentrations measured by a denatured cyanmethemoglobin method as a control method (an improvement on the international standard method for use with an automatic blood cell analyzer; using Stromatolyzer C (TOA MEDICAL ELECTRONICS CO., LTD.) and making measurement by means of K-4500) (FIG. 1). With this apparatus, the blood is diluted with the diluent, and then mixed with the above reagent. Finally, the blood is diluted 1:500, and the concentrations of the cationic surfactants, EDTA-2K and phosphate buffer in the reagent drop to ⅓. NaCl is contained in the diluent as well, and the electric conductivity is almost unchanged. In the drawing, the X axis represents the conventional method, while the Y axis represents the method using the reagent of the present invention. A high correlation was obtained (correlation coefficient r=0.997, regression line Y=0.951X+0.588), confirming that hemoglobin was measurable using the reagent of the present invention.

2) Correlation in Leukocytes

Figure 2:
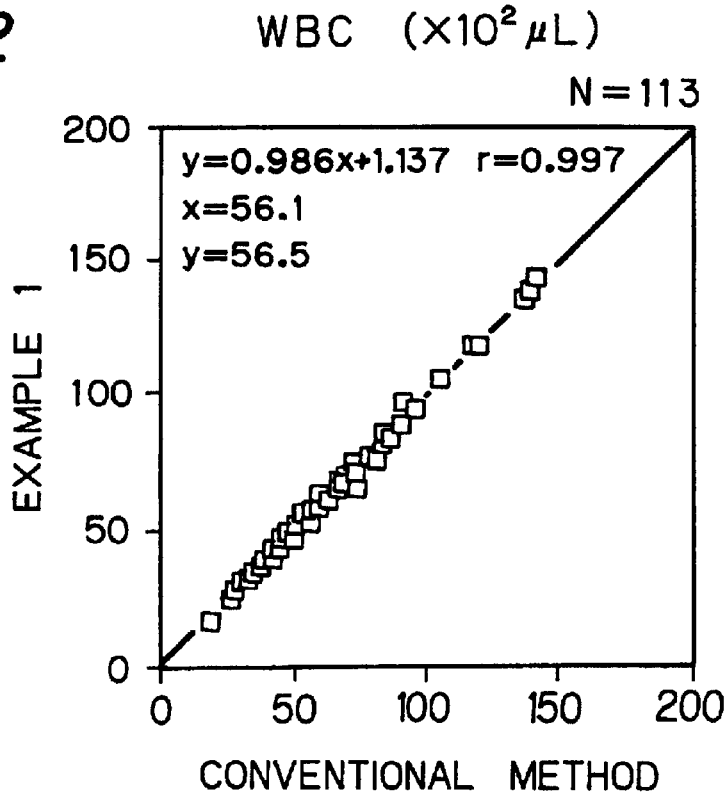
FIG. 2 is a graph showing the correlation between the leukocyte count measured by the use of the reagent of the present invention and the leukocyte count measured by a conventional method.

The leukocyte counts were measured in 113 samples with the use of the above reagent, Cellpack™ (TOA MEDICAL ELECTRONICS CO., LTD.) as a diluent, and K-4500 (TOA MEDICAL ELECTRONICS CO., LTD.). A graph was drawn for showing the correlation of the results with the leukocyte counts measured by a control method using Stromatolyzer 3WP™ (TOA MEDICAL ELECTRONICS CO., LTD.) and making measurement by means of K-4500 (FIG. 2). A high correlation was obtained (correlation coefficient r=0.997, regression line Y=0.986X+1.137), confirming that leukocytes were measurable as with the conventional method.

Figure 3:
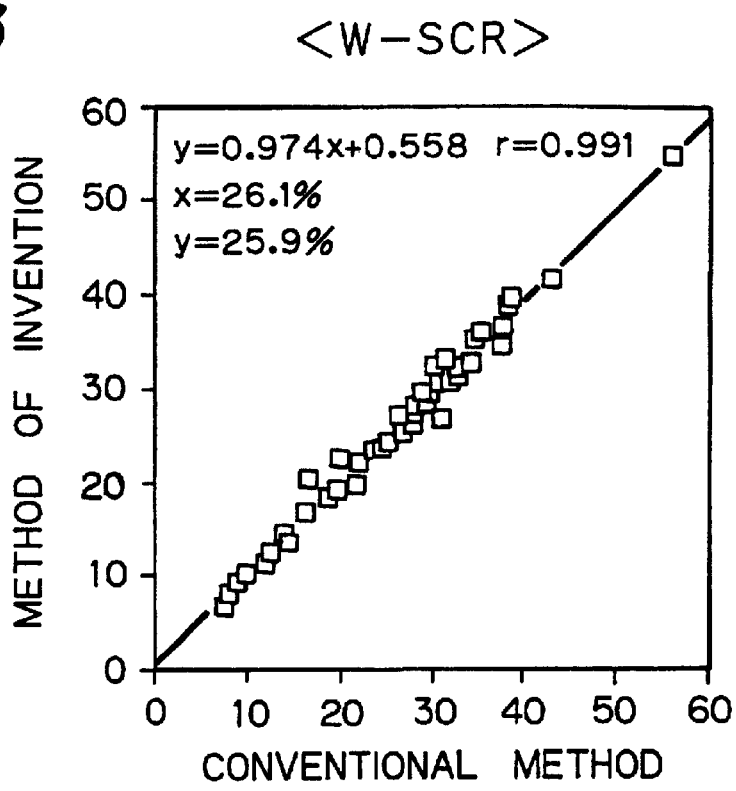
FIG. 3 is a graph showing the correlation between the W-SCR measured by the use of the reagent of Example 2 and the W-SCR measured by a conventional method.
Figure 4:
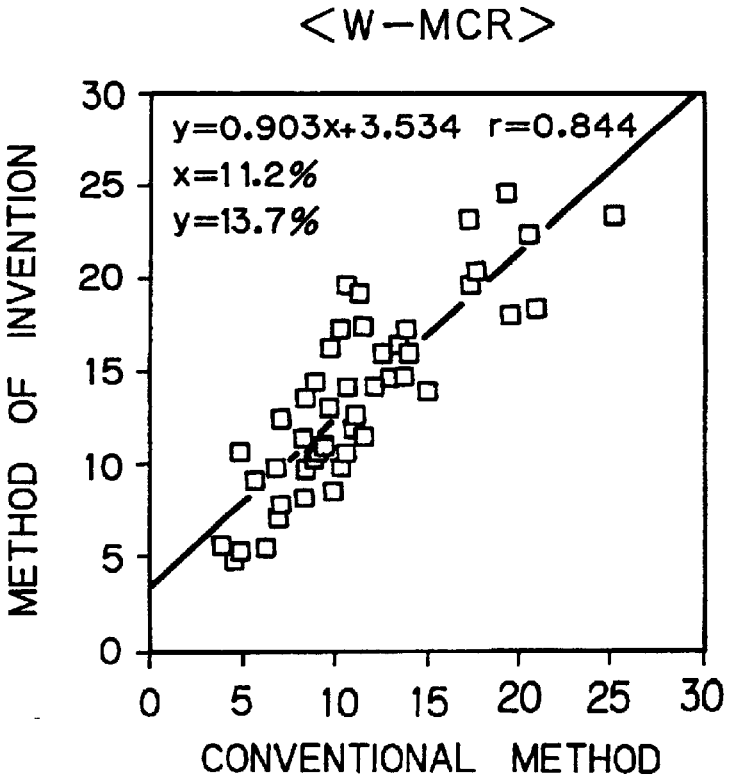
FIG. 4 is a graph showing the correlation between the W-MCR measured by the use of the reagent of Example 2 and the W-MCR measured by a conventional method.
Figure 5:
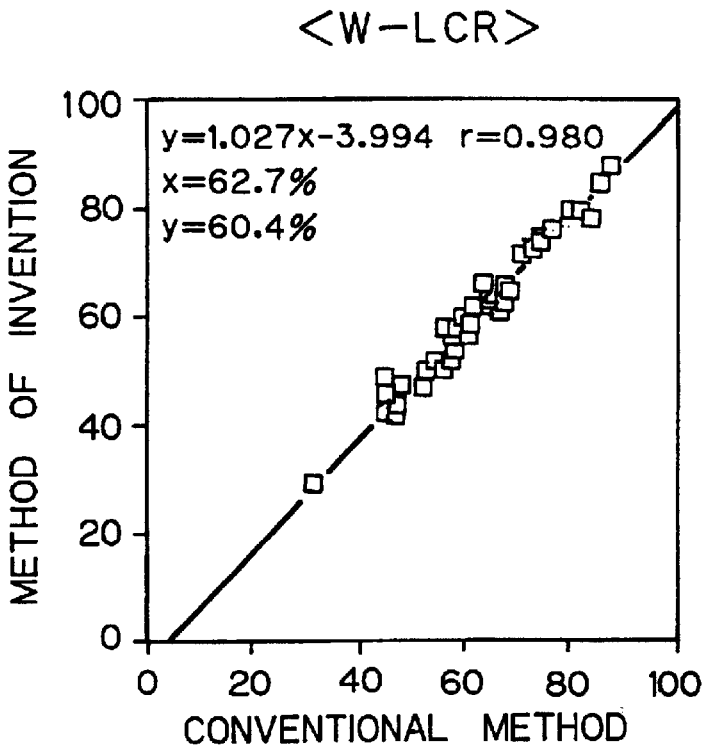
FIG. 5 is a graph showing the correlation between the W-LCR measured by the use of the reagent of Example 2 and the W-LCR measured by a conventional method.
Figure 6:
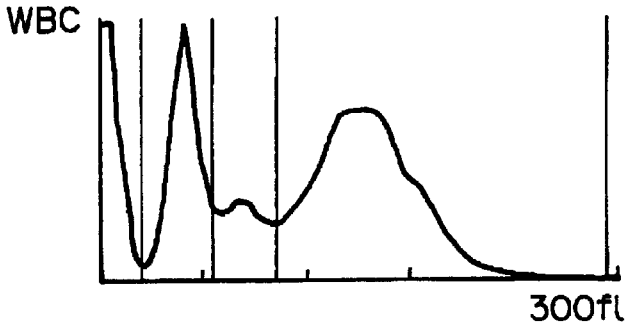
FIG. 6 is a graph showing the particle size distribution of leukocytes measured by the use of the reagent of Example 2.

The differential leukocyte counts were also studied in 51 samples, and as high a correlation as with the conventional method was obtained. The results are shown in FIGS. 3 to 5. The W-SCR represents the ratio of small leukocytes after addition of a hemolytic agent, and this ratio corresponds to the ratio of lymphocytes. The W-LCR represents the ratio of large leukocytes after addition of a hemolytic agent, corresponding to the ratio of neutrophils. The W-MCR represents the ratio of medium-sized leukocytes after addition of a hemolytic agent, corresponding to the ratio of other leukocytes. A graph showing the particle size distribution of the leukocytes is given as FIG. 6.

EXAMPLE 3

Reagent for Classification of Leukocytes into Two Types

| Composition of reagent | |
|---|---|
| Lauryltrimethylammonium chloride | 6.1 g/L |
| Stearyltrimethylammonium chloride | 1.1 g/L |
| EDTA-2K | 3.0 g/L |
| Phosphate buffer | 60 mM (pH 5.0) |
| NaCl | Such an amount that the electric conductivity is about 13 mS/cm) |
| Purified water | 1 L |

Figure 7:
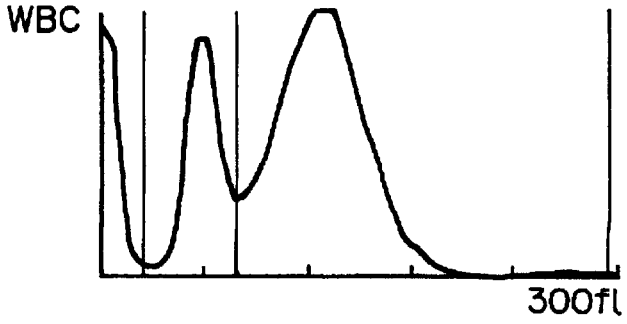
FIG. 7 is a graph showing the particle size distribution of leukocytes measured by the use of the reagent of Example 3.

Leukocytes were measured with the use of the above reagent, Cellpack™ (TOA MEDICAL ELECTRONICS CO., LTD.) as a diluent, and K-4500 (TOA MEDICAL ELECTRONICS CO., LTD.). It was confirmed that this method was able to classify leukocytes into two populations. A graph showing the particle size distribution of the leukocytes is given as FIG. 7. In the drawing, the population with a smaller particle size corresponds to lymphocytes, while the population with a larger particle size corresponds to other leukocytes.

As noted above, according to the present invention, the leukocyte count and the hemoglobin concentration can be measured stably even when the liquid temperature of the blood sample is changed. Thus, a unit for keeping the liquid temperature of the blood sample constant is not required, and the cost of an analyzer can be reduced Also, the leukocyte count and the hemoglobin concentration can be measured without the use of a cyanogen compound, so that a special procedure for liquid waste treatment becomes unnecessary.

What is claimed is:

1. A reagent for measurement of leukocytes and hemoglobin concentration in blood, said reagent consisting essentially of:

(1) a cationic surfactant in an amount sufficient to lyse erythrocytes and denature hemoglobin, (2) at least one hemoglobin stabilizer selected from the group consisting of the following (a), (b) and (c):

(a) sulfosalicylic acid, or its salt, in an amount effective for promoting the conversion of hemoglobin into methemoglobin, (b) 0.2 to 10.0 g/L of a water-soluble chelating agent having a nitrogen atom and a carboxyl group, and (c) piperazine, or its salt, in an amount effective for promoting the conversion of hemoglobin into methemoglobin, and (3) a buffer for maintaining pH at 4 to 6.

2. The reagent as claimed in claim 1, wherein said water-soluble chelating agent is a salt of EDTA.

3. The reagent as claimed in claim 1, wherein the amount effective for promoting the conversion of hemoglobin into methemoglobin is 0.2 to 10.0 g/L for sulfosalicylic acid or its salt, and 0.2 to 10.0 g/L for piperazine or its salt.

4. A reagent for measurement of blood leukocyte counts and hemoglobin concentrations by conversion to methemoglobin, said reagent containing:

(1) a cationic surfactant in an amount effective to lyse erythrocytes and denature hemoglobin, (2) at least one or more hemoglobin stabilizers present in a total amount sufficient to convert the hemoglobin to methemoglobin, said at least one or more stabilizers being selected from the group consisting of the following (a), (b) and (c):

(a) sulfosalicylic acid or its salt, (b) 0.2 to 10.0 g/L of a water-soluble chelating agent having a nitrogen atom and a carboxyl group, and (c) piperazine or its salt, and (3) a buffer for maintaining pH at 4 to 6.

*5. A reagent for measurement of blood leukocyte counts and hemoglobin concentration in blood, said reagent consisting essentially of:*

*(1) one or more cationic surfactants in an amount effective to lyse erythrocytes and denature hemoglobin,*

*(2) 0.2 to 10.0 g/L of a water soluble chelating agent having a nitrogen atom and a carboxyl group, and*

*(3) a buffer for maintaining pH at 4 to 6.*

*6. A reagent for measurement of blood leukocyte counts and hemoglobin concentrations by conversion to methemoglobin, said reagent comprising:*

*(1) one or more cationic surfactants in an amount effective to lyse erythrocytes and denature hemoglobin,*

*(2) 0.2 to 10.0 g/L of a water soluble chelating agent having a nitrogen atom and a carboxyl group, said chelating agent being present in a total amount sufficient to convert the hemoglobin to methemoglobin, and*

*(3) a buffer for maintaining pH at 4 to 6.*

* * * * *